United States Patent
Yamamoto et al.

(10) Patent No.: US 6,288,128 B1
(45) Date of Patent: *Sep. 11, 2001

(54) β,γ-DIHYDROPOLYPRENYL ALCOHOL DERIVATIVES AND PHARMACEUTICAL COMPOSITION CONTAINING A POLYPRENYL COMPOUND

(75) Inventors: Masaichi Yamamoto, Tokyo; Seiichi Araki; Hiroshi Yamamoto, both of Gifu; Isao Yamatsu, Ibaragi; Takeshi Suzuki, Ibaragi; Akiharu Kajiwara, Ibaragi; Yoshikazu Suzuki, Ichinomiya; Haruyoshi Arai, Inuyama, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/601,489

(22) Filed: Feb. 14, 1996

Related U.S. Application Data

(63) Continuation of application No. 08/436,801, filed on May 5, 1995, now abandoned, which is a continuation of application No. 08/201,191, filed on Feb. 24, 1994, now abandoned, which is a division of application No. 08/011,197, filed on Jan. 29, 1993, now Pat. No. 5,280,048, which is a division of application No. 07/617,939, filed on Nov. 26, 1990, now abandoned, which is a division of application No. 07/183,488, filed on Apr. 8, 1988, now abandoned, which is a division of application No. 07/086,186, filed on Aug. 13, 1987, now abandoned, which is a continuation of application No. 06/498,235, filed on May 26, 1983, now abandoned, which is a division of application No. 08/144,197, filed on Oct. 27, 1993, now abandoned.

(30) Foreign Application Priority Data

| May 28, 1982 | (JP) | 57-89806 |
| Jun. 22, 1982 | (JP) | 57-106203 |
| Oct. 21, 1982 | (JP) | 57-183642 |
| Oct. 21, 1982 | (JP) | 57-183643 |

(51) Int. Cl.$^7$ .......... A61K 31/045; A61K 31/08; A61K 31/12

(52) U.S. Cl. .......... 514/739; 514/722; 514/675; 514/546; 514/544

(58) Field of Search .......... 514/739, 724, 514/722, 675, 546, 544

(56) References Cited

U.S. PATENT DOCUMENTS

| 4,169,157 | * | 9/1979 | Kijima et al. | 514/675 |
| 4,186,211 | * | 1/1980 | Debst | 514/724 |
| 4,325,974 | * | 4/1982 | Yamatsu et al. | 514/739 |
| 4,624,966 | * | 11/1986 | Yamamoto et al. | 514/724 |
| 4,954,525 | * | 9/1990 | Yamatsu et al. | 514/675 |
| 5,427,775 | * | 6/1995 | Sakai et al. | 514/675 |

OTHER PUBLICATIONS

Bioscience Reports 1, 893–902 (1981), Izabella Krajewska and W. Jankowski, Institute of Biochemistry and Biophysics, Polish Academy of Sciences.

* cited by examiner

Primary Examiner—C. S. Aulakh
(74) Attorney, Agent, or Firm—Flynn, Thiel, Boutell & Tanis, P.C.

(57) ABSTRACT

A β,γ-dihydropolyprenyl alcohol derivative having the formula:

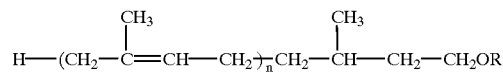

wherein n is an integer of 5 to 7 and R is hydrogen, a lower alkyl group or an aliphatic or aromatic acyl group, is new and useful as a prophylactic therapeutic agent for human and animal immuno-deficiency deseases and phylactic agent against human and animal infectious deseases. Another disclosed polyprenyl compound is also useful as the same agent.

1 Claim, No Drawings

β,γ-DIHYDROPOLYPRENYL ALCOHOL DERIVATIVES AND PHARMACEUTICAL COMPOSITION CONTAINING A POLYPRENYL COMPOUND

This application is a continuation of U.S. Ser. No. 08/436,801, filed May 5, 1995 abandoned, which is a continuation of Ser. No. 08/201,191, filed Feb. 24, 1994 abandoned, which is a division of Ser. No. 08/144,197, filed Oct. 27, 1993 abandoned, which is a division of Ser. No. 08/011,197, filed Jan. 29. 1993 now U.S. Pat. No. 5,280,048, which is a division of Ser. No. 07/617,939, filed Nov. 26, 1990 abandoned, which is a division of Ser. No. 07/183,488, filed Apr. 8, 1988 abandoned, which is a division of Ser. No. 07/086,186, filed Aug. 13, 1987 abandoned, which is a continuation of Ser. No. 06/498,235, filed May 26. 1983 abandoned.

This invention relates to a novel β,γ-dihydropolyprenyl alcohol derivatives having the formula (I), a process for preparing the same and a pharmaceutical composition containing a polyprenyl compound having the formula XI, XII or XIII or another polyprenyl compound, which is useful as a prophylactic therapeutic agent for human and animal immuno-deficiency diseases and a phylactic agent against human and animal infectious diseases.

(I)

wherein n is an integer of 5 to 7 and R is a hydrogen atom, a lower alkyl group or an aliphatic or aromatic acyl group.

In this formula (I), the lower alkyl group in the definition of R means $C_1$ to $C_6$ straight-chain or branched alkyl groups such as methyl, ethyl, n-propyl, isopropyl, n-butyl, isobutyl, 1-methylpropyl, tert-butyl, n-pentyl, 1-ethylpropyl, isoamyl and n-hexyl.

The novel compound having the formula (I) can be prepared by various methods and some typical examples will be given.

Method of Preparation 1

(a) The compound represented by the following general formula [II] is reacted with an alkyl cyanoacetate in the presence of a base to obtain a compound represented by the following general formula [III]:

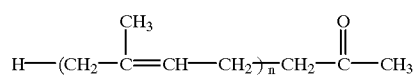
[II]

wherein n is an integer of 5 to 7;

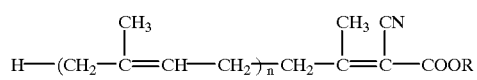
[III]

wherein n is an integer of 5 to 7 and R is a lower alkyl group.

(b) The resulting compound of formula [III] is reduced using a reducing agent such as sodium borohydride to obtain a compound represented by the following general formula [IV]:

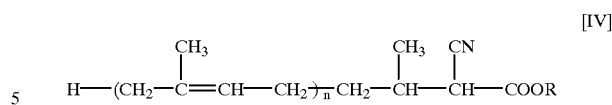
[IV]

wherein each of n and R has the meaning as defined above.

(c) The resulting compound of formula [IV] is subjected to ester and nitrile hydrolysis in the presence of a strong alkali such as potassium hydroxide to obtain a compound represented by the following general formula [V]:

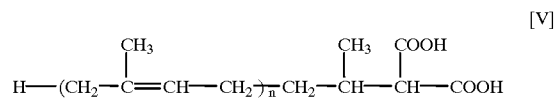
[V]

wherein n has the same meaning as defined above.

(d) The resulting compound of formula [V] is decarboxylated in the presence of pyridine/copper, for example, to obtain a compound represented by the following general formula [VI]:

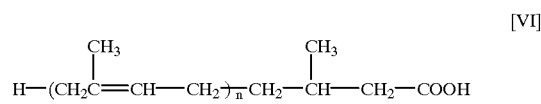
[VI]

wherein n has the same meaning as defined above.

(e) The resulting compound of formula [VI] is reduced using a reducing agent such as lithium aluminum hydride, vitrite, sodium bis(2-methoxyethoxy)aluminum hydride or the like, providing one of the intended compounds of the general formula [I]:

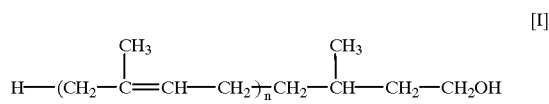
[I]

wherein n has the same meaning as defined already.

(f) The alcoholic hydroxyl group of the compound of formula [I] is converted into an active group such as a tosyl or mesyl group and the compound is reacted with a corresponding alkyl alcohol in the presence of a base such as caustic potash to give its alkyl ether. Its ester also can be derived by reacting the compound with a corresponding aliphatic or aromatic acyl chloride or acid anhydride.

Method of Preparation 2

A compound represented by the following general formula [II] is subjected to the Wittig-Homer reaction together with triethylphosphonoacetic acid in the presence of a base to obtain a compound represented by the following general formula [VII]:

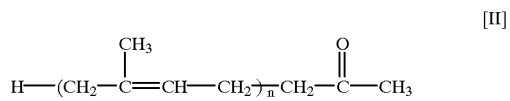
[II]

wherein n is an integer of 5 to 7;

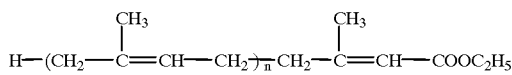

wherein n has the same meaning as defined already.

The resulting compound of formula [VII] is hydrolyzed using a base such as caustic potash to obtain a compound represented by the following general formula [VIII]:

wherein n has the same meaning as defined already.

The compound of formula [VIII] is then reduced using metallic sodium or the like to obtain a compound represented by the following general formula [VI]:

The corresponding alcohol and its derivative can be derived by following the procedures of Method of Preparation 1.

Method of Preparation 3

A compound represented by the following general formula [II] is subjected to the Witting-Hormer reaction together with diethylphosphonoacetonitrile in the presence of a base to obtain a compound represented by the following general formula [IX]:

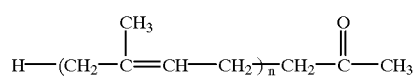

wherein n is an integer of 5 to 7;

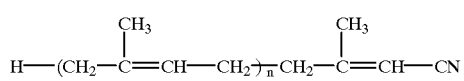

wherein n has the same meaning as defined above.

The resulting compound of formula [IX] is reduced using a reducing agent such as metallic magnesium in a mixed solvent such as methanol/THF to obtain a compound represented by the following general formula [X]:

wherein n has the same meaning as defined above.

Next, the compound of formula [X] is hydrolyzed using caustic potash, for example, to obtain a compound represented by the following general formula [VIII]:

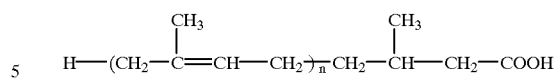

Thereafter, the procedures of Example of Preparation 1 are followed to derive the corresponding alcohol and its derivative.

The invention further provides a pharmaceutical composition which comprises a pharmaceutically acceptable carrier and a pharmaceutically effective amount of a polyprenyl compound selected from the group consisting of polyprenyl compounds having the following formulae:

wherein n is an integer of 5 to 7 and R is a lower alkyl group or an aliphatic or aromatic acyl group;

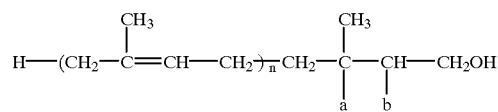

wherein each of a and b is hydrogen or a and b are combined together to form a bond, and n is an integer of 1 to 10;

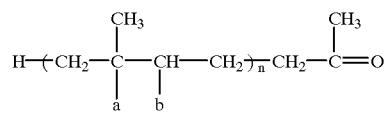

wherein each of a and b is hydrogen or a and b are combined together to form a bond and n is an integer of 1 to 10; 3,7,11,15-tetramethylhexadeca-1-en-3-ol; 3,7,11,15-tetramethyl-1,6,10,14-hexadecatetraen-3-ol; docosanol; phytol and iso-phytol.

In other words, the above defined pharmaceutical composition contains as the effective ingredient the novel β,γ-dihydropolyprenyl alcohol derivative as mentioned before or another polyprenyl compound.

All the above defined pharmaceutical compositions are effective as a prophylactic, therapeutic agent for human and animal immuno-deficiency diseases. Moreover, especially the composition containing the polyprenyl compound having the formula XII or XIII is useful as a phylactic agent against human and animal infectious diseases.

Immunology has made a remarkable progress in recent years and various diseases are now believed to originate from immunodeficiency. For example, cancer, microbism, asthma, rheumarthritis and autoimmune disease can be cited as the diseases resulting from immunodeficiency.

In addition to simple microbism due to mere invasion of pathogenic bacteria, the increase of the complicated microbism involving various fundamental troubles has become a serious problem. The microbism induced by cancer, for example, is one of the most troublesome clinical problems. Cancer triggers the drop of general and local resistance and complicating and secondary diseases occur in an easily infective state. Infection due to cancer mostly, assumes the form of infection through a respirator, a urinary passage, a placental passage and a skin at the initial stage and results mostly in pneumonia and sepsis at the final stage. The mechanism of coincidence of infection due to this tumor takes generally the following process.

With the progress of leukemia, malignant lymphoma or cancer, the function of normal tissue and cells, especially that of lymphatic cells and granulocyte cells is reduced so that a patient is easily infected and infectious diseases occur coincidently. In such a case, the dose of antibiotics does not result in radical cure but mostly in such problems as repeated infection, microbial substitution or refractory infection. Accordingly, radical cure can not be expected by use of the conventional antibiotics and chemotherapeutic agents but can be obtained only after a biophylactic function is improved. Hence, development of drugs for improving the biophylactic function of organism has been earnestly awaited.

On the other hand, antibiotics have been used primarily to cure bacterial infection of animals such as livestock and poultry and, as a matter of fact, various antibiotics have reduced the number or kinds of serious infectious diseases due to pathogenic bacteria. In the livestock industry, however, the abuse of antibiotics has caused a serious social problem such as residual drugs in various products, increase of drug-resistant bacteria and microbial substitution. In other words, the phylactic power of host is reduced remarkably and a restorative function against infectious diseases is also impaired so that the microbism is difficult to cure and the host is liable to suffer from reinfection. Furthermore, spontaneous infectious diseases (opportunistic infection) reduce the producibility of livestock and its loss is great. Hence, the immunological competence of the host and the biophylactic function must be enhanced.

Under these circumstances, the inventors of the present invention have made intensive studies in search of drugs that normalize an immunological function and enhance a biophylactic function, and have found unexpectedly that a polyprenyl compound as defined above is effective as a prophylactic/therapeutic agent for human and animal immuno-deficiency diseases and especially as a phylactic agent against human and animal infectious diseases:

In other words, the compound of the present invention is effective in normalizing human and animal immunological functions and enhancing resistance against infection. Hence, the compound is useful as a prophylactic/therapeutic agent for human and animal immunodeficiency diseases and as a phylactic agent against a variety of infectious diseases.

For man, the compound of the present invention is effective for rheumarthritis, autoimmune disease, cancer, asthma, various infectious diseases such as sepsis, pneumonia, meningitis and other viral infectious diseases.

For animals, the compound of the present invention is effective for swine diarrhea, pneumonia (SEP, AR, haemophilus, pasteurella) and TGE, avian pneumonia (mycoplasma, haemophilus) and Marek's diseases, and bovine diarrhea, pneumonia and mastitis.

In curing human and animal infectious diseases by the compound of the present invention, the therapeutic effect can be improved remarkably by the use of the present compound in combination with antibiotics. This is significant because the aforementioned social problem of the abuse of antibiotics can also be solved.

In the case of animals such as livestock and poultry, the compound of the present invention enhances the resistance of organisms against infection and hence the compound is effective as a basal drug for newborn. Furthermore, it is effective for mitigating the stress resulting from mass raising, transportation, and the like and is also useful for improving the vaccinal effect.

Accordingly, it is another purpose of the present invention to provide a novel prophylactic/therapeutic composition for human and animal immunodeficiency.

It is further purpose of the present invention to provide a novel phylactic composition against human and animal infectious diseases.

The following compounds are typical examples of polyprenyl alcohols having the formulae (XI) and (XII), but it is to be noted that they are merely illustrative but not limitative in any manner.

3,7,11,15,19,23,27,31-octamethyl-2,6,10,14,18,22,26,30-dotriacontaoctaen-1-ol 3,7,11,15,19,23,27,31,35-nonamethyl-2,6,10,14,18,22,26,30,34-hexatriacontanonaen-1-ol 3,7,11,15,19,23,27,31,35,39-decamethyl-2,6,10,14,18,22,26,30,34,38-tetracontadecaen-1-ol 3,7,11,15,19,23,27,31,35,39,43-undecamethyl-2,6,10,14,18,22,26,30,34,38,42-tetratetracontaundecaen-1-ol 3,7,11,15,19,23,27-heptamethyl-2,6,10,14,18,22,26-octacosaheptaen-1-ol 3,7,11,15,19,23-hexamethyl-2,6,10,14,18,22-tetracosahexaen-1-ol 3,7,11,15,19-pentamethyl-2,6,10,14,18-eicosapentaen-1-ol 3,7,11,15-tetramethyl-2,6,10,14-hexadecatetraen-1-ol 3,7,11-trimethyl-2,6,10-dodecatrien-1-ol 3,7-dimethyl-2,6-octadien-1-ol 3,7,11,15,19,23,27,31,35-nonamethyl-6,10,14,18,22,26,30,34-hexatriacontaoctaen-1-ol 3,7,11,15,19,23,27,31,35,39-decamethyl-6,10,14,18,22,26,30,34,38-tetracontanonaen-1-ol 3,7,11,15,19,23,27,31,35,39,43-undecamethyl-6,10,14,18,22,26,30,34,38,42-tetratetracontadecaen-1-ol 3,7,11,15,19-pentamethyl-6,10,14,18-eicosatetraen-1-ol 3,7,11,15-tetramethyl-6,10,14-hexadecatrien-1-ol 3,7,11-trimethyl-6,10-dodecadien-1-ol 3,7-dimethyl-6-octen-1-ol 3,7,11,15,19,23-hexamethyl-6,10,14,18,22-tetracosapentaen-1-ol 3,7,11,15,19,23,27-heptamethyl-6,10,14,18,22,26-octacosahexane-1-ol 3,7,11,15,19,23,27,31-octamethyl-6,10,14,18,22,26,30-dotriacontaheptaen-1-ol The compound having the formulae [XI] and [XII] can be prepared by various methods. When a and b in the general formula [XII] are combined together to form a bond, the compound can be prepared by those methods which are disclosed by Burrell et al. in J. Chem. Soc. (C), 1966, 2144, Popjak et al. in J. Biol. Chem., 237, 56 (1962), O. Isler et al. in Helv. Chim. Acta, 32, 2616 (1956), Japanese Patent Laid-Open No. 31610/1978, and Japanese Patent Laid-Open No. 55506/1979, for example.

When a and b are both hydrogen atoms in the formula [XII], the compound and the compound having the formula [XI] can be prepared by the method disclosed in Japanese Patent Laid-Open No. 76829/1980, for example. This method will be described more definitely.

(a) A lower alkyl cyanoacetate is reacted with a compound of the formula [II]

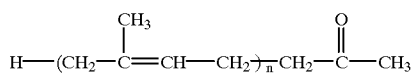
[II]

(wherein n is an integer of 1 to 10) in the presence of a base to obtain a compound represented by the formula [III]:

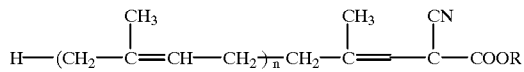
[III]

(wherein n has the same meaning as above and R is a lower alkyl group).

(b) The resulting compound of formula [III] is reduced by a reducing agent such as sodium borohydride to obtain a compound represented by the formula [IV]:

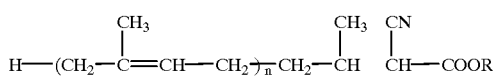
[IV]

(wherein n and R have the same meaning as above).

(c) The resulting compound of the formula [IV] is decarboxylated in the presence of a strong alkali such as potassium hydride to obtain a compound represented by the formula [XV]:

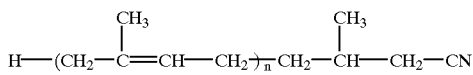
[XV]

(wherein n has the same meaning as above).

(d) The resulting compound of the formula [XV] is hydrolyzed in the presence of a strong alkali such as potassium hydroxide to obtain a compound represented by the formula [XVI]:

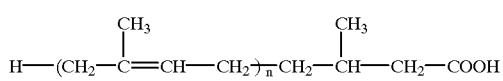
[XVI]

(e) The intended compound of the formulae [XI] and [XII] where a and b are hydrogen can be prepared by reducing the resulting compound of the formula [XVI] using a reducing agent such as vitrite, lithium aluminum hydride, or the like:

(wherein n is an integer of 1 to 10).

The compound having the formula [XIII] is illustrated as follows:
6,10,14-trimethyl-5,9,13-pentadecatrien-2-one
6,10,14,18-tetramethyl-5,9,13,17-nonadecatetraen-2-one
6,10,14,18,22-pentamethyl-5,9,13,17,21-tricosapentaen-2-one
6,10,14,18,26-hexamethyl-5,9,13,17,21,25-heptacosahexaen-2-one
6,10,14,18,22,26,30-heptamethyl-5,9,13,17,21,25,29-hentriacontaheptaen-2-one
6,10,14,18,22,26,30,34-octamethyl-5,9,13,17,21,25,29,33-pentatriacontaoctaen-2-one
6,10,14,18,22,26,30,34,38-nonamethyl-5,9,13,17,21,25,29,33,37-nonatriacontanonaen-2-one
6,10,14,18,22,26,30,34,38,42-decamethyl-5,9,13,17,21,25,29,33,37,41-tritetracontadecaen-2-one
6,10-dimethyl-5,9-undecadien-2-one
6-methyl-5-hepten-2-one
6,10,14,18,22,26,30,34,38,42-decamethyltritetracontan-2-one
6,10,14,18,22,26,30,34,38-nonamethylnonatriacontan-2-one
6,10,14,18,22,26,30,34-octamethylpentatriacontan-2-one
6,10,14,18,22,26,30-heptamethylhentriacontan-2-one
6,10,14,18,22,26-hexamethylheptacosan-2-one
6,10,14,18,22-pentamethyltricosapentan-2-one
6,10,14,18-tetramethylnonadecan-2-one
6,10,14-trimethylpentadecan-2-one
6,10-dimethylundecan-2-one
6-methylheptan-2-one Though the compound of the formula [XIII] can be prepared by various methods, one of the ordinary methods is as follows:

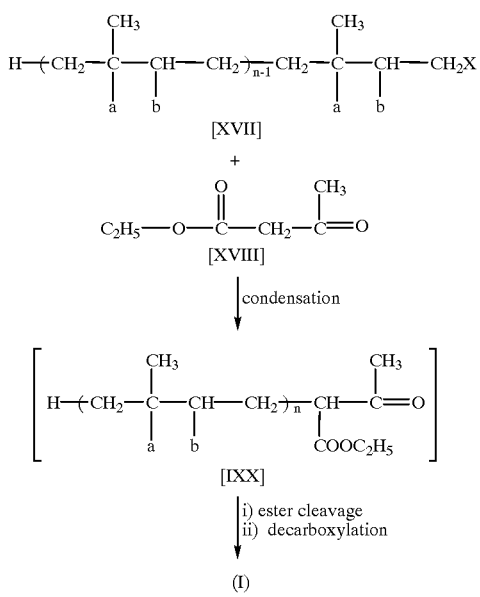

wherein each of a, b and n has the same meaning as defined already, and X is a halogen atom.

In other words, prenyl halide represented by the general formula [XVII] and ethyl acetoacetate [XVIII] are reacted in the presence of a condensing agent such as metallic sodium, metallic potassium, sodium ethylate, sodium hydrate or the like in a solvent such as ethanol, t-butanol, dioxane, benzene or the like, whenever necessary, to effect condensation. The resulting condensate is generally treated with an alkali reagent such as a dilute aqueous caustic soda solution, a dilute aqueous caustic potash solution or the like without isolating the condensate, so as to effect ester cleavage and decarboxylation and thus obtain the intended compound of formula [XIII].

The following are examples of the novel compound according to the present invention. However, these examples are merely illustrative but not limitative in any manner.

EXAMPLE 1

3,7,11,15,19,23-Hexamethyl-6,10,14,18,22-tetracosapentaenol 40 g of 6,10,14,18,22,26-hexamethyl-5,9,13,17,21,25-heptacosahexaen-2-one, 15 g of ethyl cyanoacetate, 15 g of acetic acid and 500 ml of acetone were mixed, refluxed at 84 to 85° C. and subjected to dehydrocondensation with stirring. After reacting for 7 hours, the reaction product was washed with water and an organic layer was isolated. While the residue was cooled by ice and stirred, 100 ml of an ethanol solution containing 13 g of sodium borohydride was added. After the reduction was completed, the excessive reducing agent was decomposed by 10% acetic acid, washed with water and concentrated. The concentrate was dissolved in 200 ml of propylene glycol. After 26 g of caustic potash was added, the solution was stirred at 160° C. for 3 hours. The reaction solution was cooled by ice and after 100 ml of 6N hydrochloric acid was added, it was extracted with n-hexane. After the organic layer was washed with water and dried, the product was concentrated.

42 g of a dicarboxylic acid obtained as the crude reaction product was dissolved in 200 ml of pyridine. After 1 g of copper powder was added, the solution was heated under reflux for 2 hours for decarboxylation. Pyridine was vacuum-distilled, and 100 ml of water and 300 ml of n-hexane were added. The copper powder was vacuum-filtered and 200 ml of 1N HCl was added to the filtrate. The organic layer was washed with water, then dried and thereafter concentrated.

The concentrate was refined into a colorless oily matter by silica gel column chromatography, providing 30 g of 3,7,11,15,19,23-hexamethyl-6,10,14,18,22-tetracosapentaenoic acid.

While being cooled by ice with stirring, the product was added dropwise to 300 ml of an ethereal suspension of 4 g of lithium aluminum hydride. After the suspension was continuously stirred for 30 minutes, 4 ml of water with 4 ml of a 15% caustic soda solution and 12 ml of water were sequentially added. The precipitated crystal was filtered and washed twice with 200 ml of ether. The filtrate was concentrated and the concentrate was refined into a colorless oily matter by silica gel column chromatography, providing the captioned 3,7,11,15,19,23-hexamethyl-6,10,14,18,22-tetracosapentaenol.

The physicochemical properties of the product were as follows:

Elementary analysis: as $C_{30}H_{52}O$

|  | C | H |
|---|---|---|
| calculated (%): | 84.04 | 12.23 |
| found (%): | 84.06 | 12.23 |

Infrared absorption spectrum (nujol): $v_{max}cm^{-1}$: 3,300, 2,930, 1,650, 1,450, 1,380

NMR spectrum: $\delta(CDCl_3)$: 5.07 (m, 5H), 3.65 (t, J=7 Hz, 2H), 1.8–2.2 (m, 18H), 1.67 (s, 3H), 1.59 (s, 15H), 1.1–1.8 (m, 6H), 0.90 (d, J=7 Hz, 3H).

Mass (M/E): 428

EXAMPLE 2

3,7,11,15,19,23,27-Heptamethyl-6,10,14,18,22,26-octacosahexaenol 82 g of 3,7,11,15,19,23,27-heptamethyl-2,6,10,14,18,22,26-octacosaheptaenoic acid was dissolved in 1 l of n-amyl alcohol and 74 g of metallic sodium was added portionwise while the solution was vigorously stirred. After metallic sodium was completely dissolved, the reaction solution was poured into iced water and was made acidic by adding 300 ml of 6 N hydrochloric acid. It was then extracted with 1 l of n-hexane, washed with water, dried and concentrated. 78 g of colorless, oily 3,7,11,15,19,23,27-heptamethyl-6,10,14,18,22,26-octacosahexaenoic acid was obtained as the crude product. The product was then added dropwise to 500 ml of an ethereal suspension of 10 g of lithium aluminum hydride while being cooled by ice and stirred. After stirring was continued for 30 minutes, 10 ml of water with 10 ml of a 15% caustic soda solution, and 30 ml of water were sequentially added. The precipitated crystal was filtered and washed twice with 200 ml of ether. The filtrate was concentrated and the concentrate was defined by silica gel column chromatography, providing the captioned 3,7,11,15,19,23,27-heptamethyl-6,10,14,18,22,26-octacosahexaenol as a colorless oily matter.

The physicochemical properties were as follows:

Elementary analysis: as $C_{35}H_{60}O$

|  | C | H |
|---|---|---|
| calculated (%): | 84.61 | 12.17 |
| found (%): | 84.60 | 12.18 |

Infrared absorption spectrum (nujol): $v_{max}cm^{-1}$: 3,300, 2,930, 1,650, 1,450, 1,380.

NMR spectrum: $\delta(CDCl_3)$ 5.07 (m, 6H), 3.65 (t, J=7 Hz, 2H), 1.8–2.2 (m, 22H), 1.67 (s, 3H), 1.59 (s, 18H), 1.1–1.8 (m, 6H), 0.90 (d, J=7 Hz, 3H)

Mass (M/E): 496

EXAMPLE 3

3,7,11,15,19,23,27,31-Octamethyl-6,10,14,18,22,26,30-dotriacontaheptaenol 21 g of 3,7,11,15,19,23,27,31-octamethyl-2,6,10,14,18,22,26,30-dotriacontaoctaenonitrile was dissolved in 250 ml of methanol and 100 ml of THF, and 24 g of metallic sodium was added. The reaction solution was stirred at room temperature for 30 minutes and was cooled with ice when foaming and heat generation were recognized. After the reaction solution was reacted for 2 hours, 500 ml of 6N hydrochloric acid was added and the reaction product was extracted by 500 ml of n-hexane. The organic layer was concentrated and the concentrate was refined by silica gel column chromatography, providing 16 g of 3,7,11,15,19,23,27,31-octamethyl-6,10,14,18,22,26,30-dotriacontaheptaenonitrile.

The resulting compound was dissolved in 100 ml of propylene glycol and, after 12 g of caustic potash was added, the solution was stirred at 160° C. for 3 hours. The reaction solution was cooled with ice and, after 100 ml of 6 N hydrochloric acid was added, extraction was effected using n-hexane. The organic layer was washed with water, dried and then concentrated, providing 16 g of 3,7,11,15,19,23,27,31-octamethyl-6,10,14,18,22,26,30-dotriacontaheptaenoic acid as the crude reaction product. The product was added dropwise to 200 ml of an ethereal suspension of 2 g of lithium aluminum hydride. After stirring was continued for 30 minutes, 2 ml of water with 2 ml of a 15% caustic soda solution, and 6 ml of water were sequentially added. The precipitated crystal was filtered and washed twice with 100 ml of ether. The filtrate was concentrated and the concentrate was refined by silica gel column chromatography, providing 14 g of the captioned 3,7,11,15,19,23,27,31-octamethyl-6,10,14,18,22,26,30-dotriacontaheptaenol in a white waxy form.

The physicochemical properties were as follows:
Elementary analysis: as $C_{40}H_{68}O$

|  | C | H |
|---|---|---|
| calculated (%): | 85.03 | 12.13 |
| found (%): | 85.04 | 12.12 |

Infrared absorption spectrum (nujol): $\nu_{max}cm^{-1}$: 3,300, 2,930, 1,650, 1,450, 1,380.

NMR spectrum: $\delta(CDCl_3)$:
5.07 (m, 7H), 3.65 (t, J=7 Hz, 2H), 1.8–2.2 (m, 26H), 1.67 (s, 3H), 1.59 (s, 18H), 1.1–1.8 (m, 6H), 0.90 (d, J=7 Hz, 3H),
Mass (M/E): 564

EXAMPLE 4

3,7,11,15,19,23-Hexamethyl-6,10,14,18,22-tetracosapentaenyl methyl ether 4 g of 3,7,11,15,19,23-Hexamethyl-6,10,14,18,22-tetracosapentaenol was dissolved in 20 ml of pyridine, and 10 g of p-toluenesulfonyl chloride was added. The solution was stirred at room temperature for 2 hours. 20 g of iced water was added and the solution was stirred for 30 minutes. Extraction was then made using 100 ml of n-hexane. The extract was sequentially washed with 1N hydrochloric acid and then with water, dried and concentrated. The concentrate was dissolved in 20 ml of dioxane. 10 ml of sodium methylate (a 28% methanolic solution) was added and the solution was stirred and refluxed for 4 hours. The reaction solution was cooled with ice and 50 ml of 6N hydrochloric acid was added. Extraction was then made using 200 ml of n-hexane. The organic layer was washed with water, dried and concentrated. The concentrate was refined by silica gel column chromatography, providing 3 g of the captioned 3,7,11,15,23-hexamethyl-6,10,14,18,22-tetracosapentaenyl methyl ether in a colorless oily form.

The physicochemical properties were as follows:
Elementary analysis: as $C_{31}H_{54}O$

|  | C | H |
|---|---|---|
| calculated (%): | 84.09 | 12.29 |
| found (%): | 84.09 | 12.30 |

Infrared absorption spectrum (nujol): $\nu_{max}cm^{-1}$: 2,930, 2,830, 1,650, 1,450, 1,380.

NMR spectrum: $\delta(CDCl_3)$ 5.08 (m, 5H), 3.37 (t, J=7 Hz, 2H), 3.30 (s, 3H), 1.8–2.2 (m, 18H), 1.67 (s, 3H), 1.59 (s, 15H), 1.1–1.8 (m, 5H), 0.90 (d, J=7 Hz, 3H).
Mass (M/E): 442

EXAMPLE 5

3,7,11,15,19,23,27-Heptamethyl-6,10,14,18,22,26-octacosahexaenyl acetate 3.5 g of 3,7,11,15,19,23,27-heptamethyl-6,10,14,18,22,26-octacosahexaenol was dissolved in 20 ml of pyridine, and 10 ml of acetic anhydride was added. After 20 g of iced water was added, the solution was stirred for one hour and extraction was then made using 100 ml of n-hexane. The extract was washed with 1N hydrochloric acid and then with water, dried and concentrated. The concentrate was refined by silica gel column chromatography, providing 3 g of the captioned 3,7,11,15,19,23,27-heptamethyl-6,10,14,18,22,26-octacosahexaenyl acetate in a colorless oily form.

The physicochemical properties were as follows:
Elementary analysis: as $C_{37}H_{62}O$

|  | C | H |
|---|---|---|
| calculated (%): | 82.46 | 11.60 |
| found (%): | 82.45 | 11.60 |

Infrared absorption spectrum (nujol): $\nu_{max}cm^{-1}$: 2,930, 1,735, 1,650, 1,450, 1,380.

NMR spectrum: $\delta(CDCl_3)$ 5.07 (m, 6H), 4.08 (t, J=7 Hz, 2H), 2.02 (s, 3H), 1.8–2.2 (m, 22H), 1.67 (s, 3H), 1.59 (s, 18H), 1.1–1.8 (m, 5H), 0.90 (d, J=7 Hz, 3H).
Mass (M/E): 538

EXAMPLE 6

3,7,11,15,19,23,27,31-Octamethyl-6,10,14,18,22,26,30-dotriacontaheptaenyl benzoate 3.2 g of 3,7,11,15,19,23,27,31-Octamethyl-6,10,14,18,22,26,30-dotriacontaheptanol was dissolved in 20 ml of pyridine, and 5 g of benzoyl chloride was added. The solution was stirred at room temperature for 2 hours. 20 g of iced water was added and the solution was stirred for 30 minutes. Extraction was then made using 100 ml of n-hexane. The extract was washed with 1N hydrochloric acid and then with water, dried and concentrated. The concentrate was refined by silica gel column chromatography, providing 2.7 g of the captioned 3,7,11,15,19,23,27,31-octamethyl-6,10,14,18,22,26,30-dotriacontaheptaenyl benzoate in a white waxy form.

Elementary analysis: as $C_{47}H_{72}O_2$

|  | C | H |
|---|---|---|
| calculated (%): | 84.37 | 10.85 |
| found (%): | 84.38 | 10.83 |

Infrared absorption spectrum (nujol): $\nu_{max}cm^{-1}$: 3,030, 2,930, 1,720, 1,650, 1,450, 1,380.

NMR spectrum: $\delta(CDCl_3)$ 7.20–8.15 (m, 5H), 5.07 (m, 7H), 4.36 (t, J=7 Hz, 2H), 1.8–2.2 (m, 26H), 1.67 (s, 3H), 1.59 (s, 21H), 1.1–1.8 (m, 5H), 0.90 (d, J=7 Hz, 3H).
Mass (M/E): 668

Next, the effect of the compound of the present invention will be described in detail with reference to Experimental Examples.

Experimental Examples
1. Phylactic Effect
(1) Method of Experiment
The following specimen compounds were intramuscularly administered to slc:ICR male mice (6 to 7 weeks old, weighing 22 to 30 g) in the respective amounts tabulated in Table 1. After 24 hours, *Escherichia coli* obtained clinically was subcutaneously innoculated at a rate of 2.8×10⁸/mouse. The survival ratio was determined from the number of survivors on the seventh day from infection.

(2) Specimen Compounds

Compound A

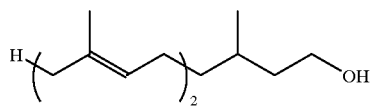

3,7,11-trimethyl-6,10-dodecadien-1-ol

Compound B

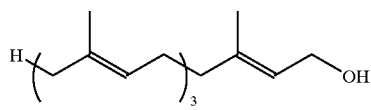

3,7,11,15-tetramethyl-2,6,10,14-hexadecatetraen-1-ol

Compound C

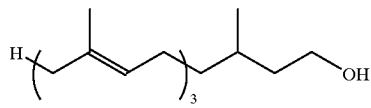

3,7,11,15-tetramethyl-6,10,14-hexadecatrien-1-ol

Compound D

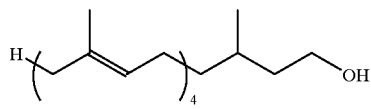

3,7,11,15,19-pentamethyl-6,10,14,18-eicosatetraen-1-ol

Compound E

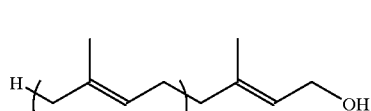

3,7,11,15,19,23,27-heptamethyl-2,6,10,14,18,22,26-octacosaheptaen-1-ol

Compound F

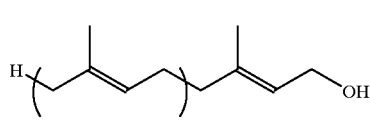

3,7-dimethyl-2,6-octadien-1-ol

Compound G

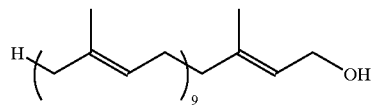

3,7,11,15,19,23,27,31,35,39-decamethyl-2,6,10,14,18,22,26,30,34,38-tetracontadecaen-1-ol Compound H

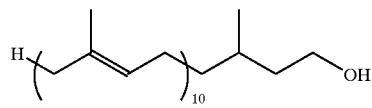

3,7,11,15,19,23,27,31,35,39,43-undecamethyl-6,10,14,18,22,26,30,34,38,42-tetratetracontadecaen-1-ol Compound I

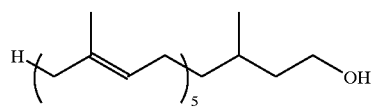

3,7,11,15,19,23-hexamethyl-6,10,14,18,22-tetracosapentaen-1-ol

Compound J

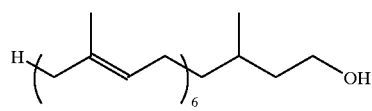

3,7,11,15,19,23,27-heptamethyl-6,10,14,18,22,26-octacosahexaen-1-ol

Compound K

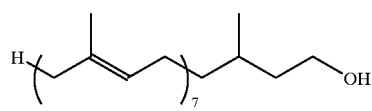

3,7,11,15,19,23,27,31-octamethyl-6,10,14,18,22,26,30-dotriacontaheptaen-1-ol

Control Compound: MDP (AcMur-L-Ala-D-Glu)

(3) Results

The results are illustrated in Table 1.

TABLE 1

| Specimen compound | Dosage | Survival ratio after one week, number of survivals/number of subjects |
| --- | --- | --- |
| compound A | 100 mg/kg | 6/10 → 60 (%) |
| compound B | 100 mg/kg | 6/10 → 60 (%) |

TABLE 1-continued

| Specimen compound | Dosage | Survival ratio after one week, number of survivals/number of subjects |
|---|---|---|
| compound C | 100 mg/kg | 7/10 → 70 (%) |
| compound D | 100 mg/kg | 6/10 → 60 (%) |
| compound E | 50 mg/kg | 9/10 → 90 (%) |
|  | 100 mg/kg | 10/10 → 100 (%) |
| compound F | 100 mg/kg | 3/10 → 30 (%) |
| compound G | 100 mg/kg | 10/10 → 100 (%) |
| compound H | 100 mg/kg | 7/10 → 70 (%) |
| compound I | 100 mg/kg | 9/10 → 90 (%) |
| compound J | 50 mg/kg | 6/10 → 60 (%) |
|  | 100 mg/kg | 10/10 → 100 (%) |
| compound K | 50 mg/kg | 5/10 → 50 (%) |
|  | 100 mg/kg | 9/10 → 90 (%) |
| blank (non-treated) |  | 1/80 → 1.25 (%) |
| control compound (MDP) | 3.5 mg/kg | 4/10 → 40 (%) |

2. Phagocytosis-enhancing Effect of Macrophage (1) Method and Results of Experiment Each specimen compound was intramuscularly administered to sic; ICR male mice (8 weeks old, weighing 22 to 30 g) at a rate of 100 mg/kg. After 24 hours, the carbon clearance test was conducted to measure the phagocytosis-enhancing effect of macrophages. The carbon clearance test was carried out in accordance with the method described by G. Biozzi, B. Benacerraf and B. N. Halpern in Brit. J. Exp. Path., 24, 441–457.

The results are shown in Table 2.

In Table 2, the value of the changes in phagocytosis represents a relative value with respect to the half-value period of the blank which was set at 100.

TABLE 2

| Specimen compound | Number of animals | Half-value period (min:sec) | Changes in phagocytosis (%) |
|---|---|---|---|
| blank (non-treated) | 48 | 8:01 | 100 |
| compound A | 4 | 5:34 | 70 |
| compound D | 4 | 5:30 | 69 |
| compound E | 4 | 5:18 | 66 |
| compound G | 3 | 6:43 | 84 |
| compound I | 4 | 5:20 | 67 |
| compound J | 4 | 5:15 | 65 |
| compound K | 4 | 3:25 | 43 |

In Table 2, when the phagocytosis is enhanced, the half-value period drops. However, at 20 (%) or more, that is, when its numeric value is smaller than 80, the phagocytosis is strongly promoted. Accordingly, among the compounds of the present invention, compounds A, D, E, I, J and K obviously have an extremely high phagocytosis-enhancing effect.

It is evident from the Experimental Examples described above that the compound of the present invention normalizes the immunological function and enhances resistance against infection.

The compound having the formula [XIII] was examined in the same way as before described.

Specimen Compounds

Compound L

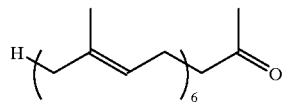

6,10,14,18,22,26-hexamethyl-5,9,13,17,21,25-heptacosahexaen-2-one

Compound M

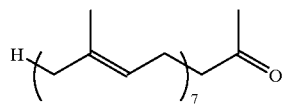

6,10,14,18,22,26,30-heptamethyl-5,9,13,17,21,25,29-hentriacontahepaten-2-one

Compound N

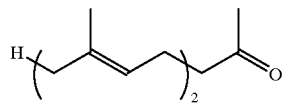

6,10-dimethyl-5,9-undecadien-2-one

Compound O

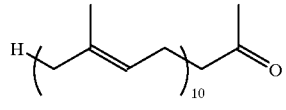

6,10,14,18,22,26,30,34,38,42-decamethyl-5,9,13,17,21,25,29,33,37,41-tritetracontadecaen-2-one Compound P

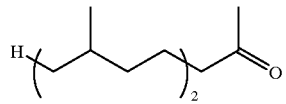

6,10-dimethylundecan-2-one

Compound Q

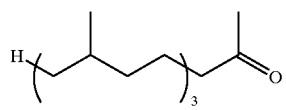

6,10,14-trimethylpentadecan-2-one
Compound R

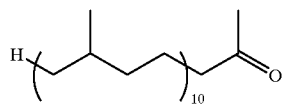

6,10,14,18,22,26,30,34,38,42-decamethyltritetracontan-2-one
Control Compound: MDP (AcMur-L-Ala-D-Glu)
Results of Experiment
The results are illustrated in Table 3.

TABLE 3

| Specimen compound | Dosage | Survival ratio after one week, number of survivors/number of subjects |
|---|---|---|
| compound L | 50 mg | 4/10 → 40 (%) |
|  | 100 mg | 9/10 → 90 (%) |
| compound M | 100 mg | 8/10 → 80 (%) |
| compound N | 100 mg | 4/10 → 40 (%) |
| compound O | 100 mg | 4/10 → 40 (%) |
| compound P | 100 mg | 8/10 → 80 (%) |
| compound Q | 100 mg | 10/10 → 100 (%) |
| compound R | 100 mg | 3/10 → 30 (%) |
| blank (non-treated) |  | 1/80 → 1.25 (%) |
| control compound (NDP) | 3.5 mg/kg | 4/10 → 40 (%) |

TABLE 4

| Specimen compound | Number of animals | Half-value period (min:sec) | Changes in phagocytosis (%) |
|---|---|---|---|
| compound L | 4 | 6:00 | 75 |
| compound M | 4 | 7:00 | 87 |
| blank (non-treated) | 48 | 8:01 | 100 |

Accordingly, compounds L and M as the typical compounds of the present invention obviously have an extremely high effect of promoting phagocytosis.

The following compounds S, T, U and V were examined in the same way as before described.
Specimen Compound
Compound S

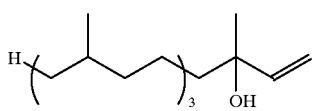

3,7,11,15tetramethylhexadeca-1-en-3-ol
Compound T

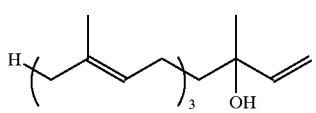

3,7,11,15-tetramethyl-1,6,10,14-hexadecatetraen-3-ol
Compound U

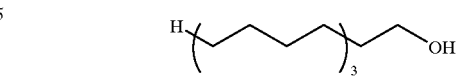

docosanol
Compound V

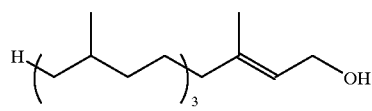

phytol
Control Compound: MDP (AcMur-L-Ala-D-Glu)
Results of Experiments
The results are illustrated in Table 5.

TABLE 5

| Specimen compound | Dosage | Survival ratio after one week number of survivors/number of subjects |
|---|---|---|
| compound S | 100 mg/kg | 10/10 → 100 (%) |
| compound T | 100 mg/kg | 10/10 → 100 (%) |
| compound U | 100 mg/kg | 3/10 → 30 (%) |
| compound V | 100 mg/kg | 10/10 → 100 (%) |
| blank (non-treated) |  | 1/80 → 1.25 (%) |
| control compound (MDP) | 3.5 mg/kg | 4/10 → 40 (%) |

TABLE 6

| Specimen compound | Number of animals | Half-value period (min:sec) | Changes in phagocytosis (%) |
|---|---|---|---|
| blank (non-treated) | 48 | 8:01 | 100 |
| compound T | 3 | 7:41 | 96 |
| compound V | 4 | 5:48 | 72 |

In Table 6, when the phagocytosis is enhanced, the half-value period drops. However, at 20 (%) or more, that is, when its numeric value is smaller than 80, the phagocytosis is strongly promoted. Accordingly, among the compounds of the present invention, compound V exhibited a particularly high phagocytosis-enhancing effect.

The compound of the present invention has extremely low toxicity and extremely high safety and can be dosed continuously for an extended period of time. In this sense, too, the compound of the present invention is highly valuable.

When the compounds (A through K) described above were perorally administered to SD rats (weighing about 200 g) at a rate of 500 mg/kg, neither death of the subjects nor side reaction were observed at all.

The dosage of the compound of the present invention as a prophylactic/therapeutic agent against human immunodeficiency diseases or as a phylactic agent against human infectious diseases varies remarkably depending upon the kind and degree of the diseases and upon the kind of the compounds is not limitative, in particular. Generally, about 10 to 4,000 mg and preferably, 50 to 500 mg per adult per day is dosed either perorally or parenterally. When the compound is dosed as a phylactic agent against infectious diseases, it may be of course dosed in combination with antibiotics. Examples of dosage forms are powder, fine particles, granules, tablets, capsules, injection, and so forth. In the preparation of the compound, the drug is prepared in a customary manner using an ordinary support.

In preparing a peroral solid preparation, for example, an excipient and, if necessary, a binder, a disintegrator, a lubricant, a coloring agent, a flavoring agent and the like are added to the principal agent and the mixture is then prepared in the form of a tablet, a coated tablet, a granule, powder, a capsule, and the like in a customary manner.

Examples of excipients are lactose, corn starch, refined sugar, glucose, sorbitol, crystalline cellulose, and the like. Examples of binders are polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, and the like. Examples of disintegrators are starch, agar, gelatin powder, crystalline cellulose, calcium carbonate, sodium hydrogencarbonate, calcium citrate, dextrin, pectin, and the like. Examples of lubricants are magnesium stearate, talc, polyethylene glycol, silica, hardened vegetable oil, and the like. Examples of coloring agents are those whose use for pharmaceuticals are officially permitted. Examples of flavoring agents are cocoa powder, menthol, aromatic powder, peppermint oil, borneol, powdered cinnamon bark, and the like. Sugar coating, gelatin coating or the like may be appropriately applied to these tablets and granules.

In preparing an injection, a pH adjuster, a buffer, a stabilizer, a preserver, a solubilizer, and the like are added to the principal agent, whenever necessary, and the injection for subcutaneous, intramuscular or intravenous injection is prepared in a customary manner.

The drug of the present invention can also be dosed to the livestock and poultry either perorally or parenterally. Peroral administration is generally effected by adding the drug to the feed. Parenteral administration can be effected by preparing an injection in a customary manner and then dosing the injection parenterally, intramascularly or intraveously.

The following are examples of preparations using 3,7,11,15,19,23,27,31-octamethyl-2,6,10,14,18,22,26,30-dotriacontaoctaen-1-ol (hereinafter referred to as the "principal agent") which is one of the compounds of the present invention.

Example of Preparation 1 (Capsule)

| principal agent | 5 g |
|---|---|
| microcrystalline cellulose | 80 g |
| corn starch | 20 g |
| lactose | 22 g |
| polyvinylpyrrolidone | 3 g |
| total | 130 g |

The components were granulated in a customary manner and were packed into 1,000 hard gelatin capsules. One capsule contained 5 mg of the principal drug.

Example of Preparation 2 (Powder)

| principal drug | 50 g |
|---|---|
| microcrystalline cellulose | 400 g |
| corn starch | 550 g |
| total | 1,000 g |

The principal agent was first dissolved in acetone, then adsorbed by microcrystalline cellulose and thereafter dried. It was then mixed with corn starch and was prepared in the powder form of 20-fold dilution.

Example of Preparation 3 (Tablet)

| principal agent | 5 g |
|---|---|
| corn starch | 10 g |
| lactose | 20 g |
| calcium carboxymethylcellulose | 10 g |
| microcrystalline cellulose | 40 g |
| polyvinylpyrrolidone | 5 g |
| talc | 10 g |
| total | 100 g |

The principal agent was first dissolved in acetone, then adsorbed by microcrystalline cellulose and thereafter dried. It was then mixed with corn starch, lactose and calcium carboxymethylcellulose and an aqueous solution of polyvinylpyrrolidone was added as a binder. The mixed solution was then granulated in a customary manner. After talc as a lubricant was added and mixed, the mixture was prepared in 100 mg tablets. One tablet contained 5 mg of the principal agent.

Example of Preparation 4 (Injection)

| principal agent | 10 g |
|---|---|
| Nikkol HCO-60 (product of Nikko Chemical Co.) | 37 g |
| sesame oil | 2 g |
| sodium chloride | 9 g |
| propylene glycol | 40 g |
| phosphate buffer (0.1M, pH 6.0) | 100 ml |
| distilled water q.s. ad | 1,000 ml |

The principal agent, Nikkol HCO-60, sesame oil and the half of propylene glycol were mixed and heat-dissolved at about 80° C. Phosphate buffer and distilled water dissolving therein in advance sodium chloride and propylene glycol were heated to about 80° C. and added to the solution described above to prepare 1,000 ml of an aqueous solution. The resulting aqueous solution was dividedly charged into 2 ml ampoules. After heat-sealed, the ampoules were heat-sterilized.

One ampoule contained 20 mg of the principal agent.

The following are examples of preparations using 3,7,11,15,19,23,27,31-octamethyl- 6,10,14,18,22,26,30-dotriacontaheptaen-1-ol (hereinafter referred to as the "principal agent") which is one of the compounds of the present invention.

Example of Preparation 5 (Capsule)

| | |
|---|---|
| principal agent | 5 g |
| microcrystalline cellulose | 80 g |
| corn starch | 20 g |
| lactose | 22 g |
| polyvinylpyrrolidone | 3 g |
| total | 130 g |

The components were granulated in a customary manner and were packed into 1,000 hard gelatin capsules. One capsule contained 5 mg of the principal drug.

Example of Preparation 6 (Powder)

| | |
|---|---|
| principal drug | 50 g |
| microcrystalline cellulose | 400 g |
| corn starch | 550 g |
| total | 1,000 g |

The principal agent was first dissolved in acetone, then adsorbed by microcrystalline cellulose and thereafter dried. It was then mixed with corn starch and was prepared in the powder form of 20-fold dilution.

Example of Preparation 7 (Tablet)

| | |
|---|---|
| principal aqent | 5 g |
| corn starch | 10 g |
| lactose | 20 g |
| calcium carboxymethylcellulose | 10 g |
| microcrystalline cellulose | 40 g |
| polyvinylpyrrolidone | 5 g |
| talc | 10 g |
| total | 100 g |

The principal agent was first dissolved in acetone, then adsorbed by microcrystalline cellulose and thereafter dried. It was then mixed with corn starch, lactose and calcium carboxymethylcellulose and an aqueous solution of polyvinylpyrrolidone was added as a binder. The mixed solution was then granulated in a customary manner. After talc as a lubricant was added and mixed, the mixture was prepared in 100 mg tablets. One tablet contained 5 mg of the principal agent.

Example of Preparation 8 (Injection)

| | |
|---|---|
| principal agent | 10 g |
| Nikkol HCO-60 (product of Nikko Chemical Co.) | 37 g |
| sesame oil | 2 g |
| sodium chloride | 9 g |
| propylene glycol | 40 g |
| phosphoric acid buffer (0.1M, pH 6.0) | 100 ml |
| distilled water total | 1,000 ml |

The principal agent, Nikkol HCO-60, sesame oil and the half of propylene glycol were mixed and heat-dissolved at about 80° C. Phosphate buffer and distilled water dissolving therein in advance sodium chloride and propylene glycol were heated to about 80° C. and added to the solution described above to prepare 1,000 ml of an aqueous solution. The resulting aqueous solution was dividedly charged into 2 ml ampoules. After heat-sealed, the ampoules were heat-sterilized.

One ampoule contained 20 mg of the principal agent.

Preparations using 6,10,14,18,22,26-hexamethyl-5,9,13,17,21,25-heptacosahexaen-2-one (hereinafter referred to as the "principal agent"), follow.

Example of Preparation 9 (Capsule)

| | |
|---|---|
| principal agent | 5 g |
| microcrystalline cellulose | 80 g |
| corn starch | 20 g |
| lactose | 22 g |
| polyvinylpyrrolidone | 3 g |
| total | 130 g |

After granulated in a customary manner, these components were charged into 1,000 hard gelatin capsules. Each capsule contained 5 mg of the principal agent.

Example of Preparation 10 (Powder)

| | |
|---|---|
| principal agent | 50 g |
| microcrystalline cellulose | 400 g |
| corn starch | 550 g |
| total | 1,000 g |

The principal agent was first dissolved in acetone, then adsorbed by microcrystalline cellulose and thereafter dried. After the dried matter was mixed with corn starch, the mixture was prepared in the powder form of 20-fold dilution of the principal agent in a customary manner.

Example of Preparation 11 (Tablet)

| | |
|---|---|
| principal agent | 5 g |
| corn starch | 10 g |
| lactose | 20 g |
| calcium carboxymethylcellulose | 10 g |
| microcrystalline cellulose | 40 g |
| polyvinylpyrrolidone | 5 g |
| talc | 10 g |
| total | 100 g |

The principal agent was first dissolved in acetone, then adsorbed by microcrystalline cellulose and thereafter dried. Corn starch, lactose and calcium carboxymethylcellulose were then added and mixed with the dried matter. After an aqueous solution of polyvinylpyrrolidone was added as a binder, the mixture was granulated in a customary manner. After talc as the lubricant was added, 100-mg tablets were prepared. Each tablet contained 5 mg of the principal agent.

Example of Preparation 12 (Injection)

| | |
|---|---|
| principal agent | 10 g |
| Nikkol HCO-60 (product of Nikko Chemical Co.) | 37 g |
| sesame oil | 2 g |
| sodium chloride | 9 g |
| propylene glycol | 40 g |

| | |
|---|---|
| phosphate buffer (0.1M, pH 6.0) | 100 ml |
| distilled water q.s. ad | 1,000 ml |

The principal agent, Nikkol HCO-60, sesame oil and the half of propylene glycol were mixed and heat-dissolved at about 80° C. Phosphate buffer and distilled water dissolving therein in advance sodium chloride and propylene glycol were heated to about 80° C. and added to the solution described above to prepare 1,000 ml of an aqueous solution. The resulting aqueous solution was dividedly charged into 2 ml ampoules. After heat-sealed, the ampoules were heat-sterilized.

One ampoule contained 20 mg of the principal agent.

The embodiments of the invention in which an exclusive property or privilege is claimed are defined as follows:

1. A pharmaceutical composition which comprises a pharmaceutically acceptable carrier and a pharmaceutically effective amount of a polyprenyl compound selected from the group consisting of polyprenyl compounds having the following formulae:

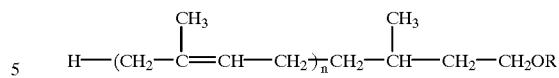

wherein n is an integer of 5 to 7 and R is a lower alkyl group or an aliphatic or aromatic acyl group;

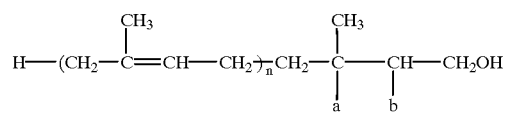

wherein each of a and b is hydrogen or a and b are combined together to form a bond, and n is an integer of 1 to 7;

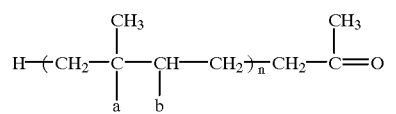

wherein each of a and b is hydrogen or a and b are combined together to form a bond, and n is an integer of 5 to 7; 3,7,11,15-tetramethylhexadeca-1-en-3-ol, 3,7,11,15-tetramethyl-1,6,10,14-hexadecatetraen-3-ol, phytol and isophytol.

* * * * *

UNITED STATES PATENT AND TRADEMARK OFFICE
CERTIFICATE OF CORRECTION

PATENT NO.   : 6,288,128 B1
DATED        : September 11, 2001
INVENTOR(S)  : Masaichi Yamamoto et al.

It is certified that error appears in the above-identified patent and that said Letters Patent is hereby corrected as shown below:

<u>Title page,</u>
Item [63], Related U.S. Application Data,
After "Feb. 24, 1994, now abandoned," insert -- which is a div of 09/144 197, filed Oct. 27, 1993, now abandoned, --.
Last lines, delete in their entirety.

Signed and Sealed this

Second Day of July, 2002

*Attest:*

*Attesting Officer*

JAMES E. ROGAN
*Director of the United States Patent and Trademark Office*